United States Patent [19]

Kraatz

[11] Patent Number: 4,876,353

[45] Date of Patent: Oct. 24, 1989

[54] PROCESS FOR THE PREPARATION OF OPTICALLY ACTIVE 2-HYDROXYETHYL-AZOLE DERIVATIVES

[75] Inventor: Udo Kraatz, Leverkusen, Fed. Rep. of Germany

[73] Assignee: Bayer Aktiengesellschaft, Leverkusen, Fed. Rep. of Germany

[21] Appl. No.: 147,415

[22] Filed: Jan. 25, 1988

[30] Foreign Application Priority Data

Feb. 3, 1987 [DE] Fed. Rep. of Germany ....... 3703082

[51] Int. Cl.$^4$ .................. C07D 249/12; C07D 233/60
[52] U.S. Cl. ...................................... 548/262; 548/341
[58] Field of Search ................................ 548/262, 341

[56]  References Cited

U.S. PATENT DOCUMENTS 4,783,538  11/1988  Kraatz et al. ...................... 548/262

FOREIGN PATENT DOCUMENTS 040345  11/1981  European Pat. Off. ............ 548/262
0181529   5/1986  European Pat. Off. .

OTHER PUBLICATIONS

Chemical Abstracts, vol. 106, No. 17, 4/27/87, Abstract 137929m, p. 642.
Journal of Organic Chemistry, vol. 52, 5/1/87, pp. 1877–1880.

*Primary Examiner*—Richard L. Raymond
*Assistant Examiner*—Patricia L. Morri
*Attorney, Agent, or Firm*—Sprung, Horn, Kramer & Woods

[57] ABSTRACT

A process for the preparation of an optically active 2-hydroxyethyl-azole derivative of the formula

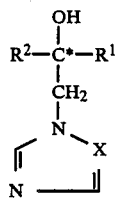
(I)

in which
X represents a nitrogen atom or a CH group, comprising
(a) in a first stage, reacting an optically active diol of the formula

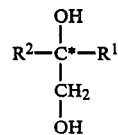
(II)

with a tosyl halide of the formula

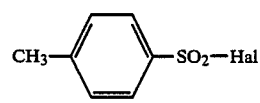
(III)

in which
Hal represents chlorine or bromine, in the presence of an acid-binding agent, thereby to produce a tosylate of the formula

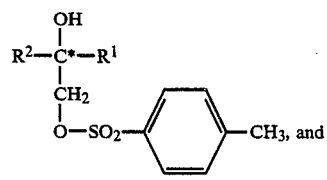
(IV)

(b) in a second stage reacting the tosylate with an azole of the formula

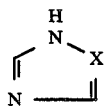
(V)

in the presence of an acid-binding agent.

9 Claims, No Drawings

PROCESS FOR THE PREPARATION OF OPTICALLY ACTIVE 2-HYDROXYETHYL-AZOLE DERIVATIVES

The present application relates to a new process for the preparation of optically active 2-hydroxyethyl-azole derivatives, some of which are known and which have a fungicidal and plant growth-regulating activity.

Racemates of numerous 2-hydroxyethyl-azole derivatived having fungicidal and plant growth-regulating properties have already been disclosed (cf. EP-OS (European Published Specification) No. 0,040,345, EP-OS (European Published Specification) No. 0,052,424 and EP-OS (European Published Specification) No. 0,084,834). However, the action of these substances is not always satisfactory, above all at low application rates.

It has furthermore beend disclosed that optically actie 2-hydroxyethyl-azole derivatives can be prepared by reacting the basic racemates of oxiranes with optically active sulphonic acids, in resolving the diastereomeric mixture produced into the pure diastereomers, and subsequently reacting the desired diastereomer in each case with azole (cf. EP-OS (European Published Specification) 0,181,529 and DE-OS (German Published Specification) 3,440,112). However, it is disadvantageous in this process that the yields of the optically active component desired in each case are relatively low since at least 50% of the material employed cannot be used due to the resolution of the diastereomer mixture.

It has now been found that optically active 2-hydroxyethyl-azole derivatives of the formula

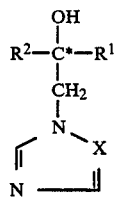
(I)

in which
R[1] represents alkyl, optionally substituted cycloalkyl, optionally substituted cycloalkylalkyl or optionally substituted aryl,
R[2] represents alkyl, alkinyl, cycloalkyl, cycloalkylalkyl, optionally substituted benzyl or the radicals of the formulae
—$CH_2$—$CH_2$—R[3], —$CH_2$—O—R[3], —C≡C—R[3] or —$CH_2$—CH=CH—R[4], where
R[3] represents optionally substituted phenyl, and
R[4] represents hydrogen or optionally substituted phenyl, and
X represents a nitrogen atom or a CH group, can be prepared in a process in which,
(a) in a first stage, optically active diols of the formula

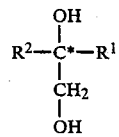
(II)

in which
R[1] and R[2] have the abovementioned meaning, are reacted with tosyl halides of the formula

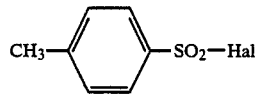
(III)

in which
Hal represents chlorine or bromine, in the presence of an acid-binding agent and if appropriate in the presence of a diluent, and
(b) in a second stage, the tosylates of the formula

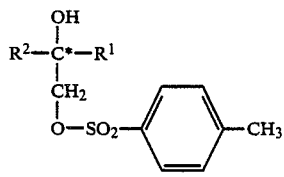
(IV)

in which
R[1] and R[2] have the abovementioned meaning, thus obtained are reacted with azoles of the formula

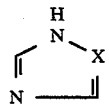
(V)

in which
X has the abovementioned meaning, in the presence of an acid-binding agent and if appropriate in the presence of a diluent.

In the present case, asymmetrically substituted carbon atoms are labelled in the formula drawings by a (*) if the compounds are optically active. Further asymmetrically substituted carbon atoms may be present in addition to the labelled carbon atoms.

The course of the process according to the invention must be described as extremely surprising. Thus, it could not have been expected that the tosylates produced as intermediates can be converted without racemization into the optically active 2-hydroxyethyl-azole derivatives of the formula (I) in a reaction with azoles. It is also unexpected that the optically active final products desired can be prepared in very good yield and high selectivity by the method according to the invention.

The process according to the invention is distinguished by a number of advantages. Thus, the starting materials and reaction components required are readily available in relatively large amounts.

Furthermore, the individual reactions and the work-up of the reaction products produced in each case present no difficulties. In addition, it should be emphasized that all the starting material is in each case converted into the desired enantiomer. Finally, a further advantage is that, through use of the appropriate starting material, both the R- and the S-enantiomers are in each case equally readily available.

If (2R)-1,2-diphenyl-propane-2,3-diol and p-tosyl chloride are used as starting materials and 1,2,4-triazole is used as a reaction component, the course of the process according to the invention may be illustrated by the following equation:

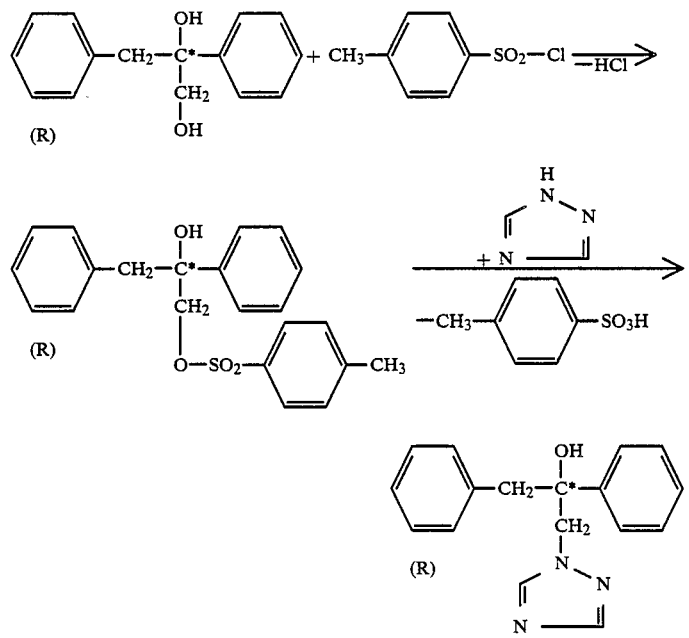

Formula (II) provides a general definition of the optically active diols required as starting materials when carrying out the process according to the invention. Preferred substances of the formula (II) are those in which $R^1$ represents alkyl having 1 to 6 carbon atoms, cycloalkyl having 3 to 8 carbon atoms which is optionally monosubstituted, disubstituted or trisubstituted by alkyl having 1 to 4 carbon atoms and/or halogen, the substituents being identical or different, cycloalkylalkyl which has 3 to 8 carbon atoms in the cycloalkyl part and 1 to 4 carbon atoms in the alkyl part and which is optionally monosubstituted, disubstituted or trisubstituted by alkyl having 1 to 4 carbon atoms and/or halogen, the substituents being identical or different, or phenyl which is optionally monosubsituted, disubstituted or trisubstituted by alkyl having 1 to 6 carbon atoms, halogen, halogenoalkyl having 1 or 2 carbon atoms and 1 to 5 halogen atoms, nitro and/or hydroxyl, the substituents being identical or different, and $R^2$ represents straight-chain or branched alkyl having 1 to 8 carbon atoms, alkinyl having 3 to 8 carbon atoms, cycloalkyl having 3 to 8 carbon atoms, cycloalkylalkyl having 3 to 8 carbon atoms in the cycloalkyl part and 1 to 4 carbon atoms in the alkyl part, benzyl which is optionally monosubstituted, disubstituted or trisubstituted in the phenyl part by alkyl having 1 to 4 carbon atoms and/or halogen, the substituents being identical or different, or the radicals of the formulae
—$CH_2$—$CH_2$—$R^3$, —$CH_2$—O—$R^3$, —C≡C—$R^3$ or —$CH_2$—CH=CH—$R^4$, where $R^3$ preferably represents phenyl which is optionally monosubstituted, disubstituted or trisubstituted by alkyl having 1 to 4 carbon atoms, alkoxy having 1 to 4 carbon atoms, halogen and/or phenyl, the substituents being identical or different, and $R^4$ preferably represents hydrogen or phenyl which is optionally monosubstituted, disubstituted or trisubstituted by alkyl having 1 to 4 carbon atoms, alkoxy having 1 to 4 carbon atoms, halogen and/or phenyl, the substituents being identical or different.

Particularly preferred R- or S- enantiomers of diols of the formula (II) are those in which $R^1$ represents alkyl having 1 to 4 carbon atoms, cycloalkyl having 3 to 6 carbon atoms which is optionally monosubstituted, disubstituted or trisubstituted by methyl, ethyl, fluorine, chlorine and/or bromine, the substituents being identical or different, cycloalkylalkyl which has 3 to 6 carbon atoms in the cycloalkyl part and 1 to 3 carbon atoms in the alkyl part and which is optionally monosubstituted, disubstituted or trisubstituted by methyl, ethyl, fluorine, chlorine and/or bromine, the substituents being identical or different, or phenyl which is optionally monosubstituted, disubstituted or trisubstituted by alkyl having 1 to 4 carbon atoms, fluorine, chloprine, bromine, trichloromethyl, trifluoromethyl, nitro and/or hydroxyl, the substituents being identical or different, and $R^2$ represents straight-chain or branched alkyl having 1 to 6 carbon atoms, alkinyl having 3 to 6 carbon atoms, cycloalkyl having 3 to 6 carbon atoms, cycloalkylalkyl having 3 to 6 carbon atoms in the cycloalkyl part and 1 to 3 carbon atoms in the alkyl part, benzyl which is optionally monosubstituted, disubstituted or trisubstituted in the phenyl part by methyl, ethyl, isopropyl, tert.-butyl, fluorine, chlorine and/or bromine, the substituents being identical or different, or the radicals of the formulae
—$CH_2$—$CH_2$—$R^3$, —$CH_2$—O—$R^3$, —C≡C—$R^3$ or —$CH_2$—CH=CH—$R^4$,
where $R^3$ preferably represents phenyl which is optionally monosubstituted, disubstituted or trisubstituted by methyl, ethyl, isopropyl, tert.-butyl, methoxy, ethoxy, fluorine, chlorine, bromine and/or phenyl, the substituents being identical or different, and R[4] preferably represents hydrogen or phenyl which is optionally monosubstituted, disubstituted or trisubstituted by methyl, ethyl, isopropyl, tert.-butyl, methoxy, ethoxy, fluorine, chlorine, bromine and/or phenyl, the substituents being identical or different.

Examples which may be mentioned of optically active diols of the formula (II) are: (2S)-1,2-diphenyl-propane-2,3-diol, (4R)-4-phenyl-pent-1-ene-4,5-diol, (4S)-4-phenyl-pent-1-ene-4,5-diol, (3R)-1-(4-chlorophenyl)-3-tert.-butyl-butane-3,4-diol, (3S)-1-(4-chlorophenyl)-3-tert.=butyl-butane-3,4-diol, (2R)-1-(4-chlorophenoxy)-2-tert.-butyl-propane-2,3-diol.

Some of the optically active diols of the formula (II) are known (cf. Tetrahedron 40, 1313 (1984)). They can be prepared by reacting optically active dioxolanones of the formula

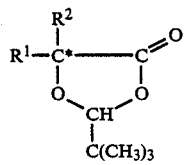  (VI)

in which
R[1] and R[2] have the abovementioned meaning, with complex hydrides, such as, for example, lithium aluminum hydride, in the presence of a diluent, such as, for example, ether, at temperatures between 0° C. and 40° C.

Configuration inversion at the center of chirality does not occur in the abovementioned reduction of the optically active dioxolanones of the formula (VI). The corresponding R-enantiomers of the formula (II) are therefore produced from the R-enantiomers of the formula (VI). Likewise, the S-enantiomers of the formula (II) are produced from the S-enantiomers of the formula (VI) by this method.

Preferred dioxolanones of the formula (VI) are the R- or S- enantiomers in which R[1] and R[2] have those meanings which have already been mentioned in connection with the description of the compounds of the formula (II) as being preferred for these radicals.

Examples which may be mentioned of optically active dixolanones of the formula (VI) are:
(2S, 5S)-2-tert.-butyl-5-benzyl-5-phenyl-1,3-dioxolan-4-one, (2R, 5R)-2-tert.-butyl-5-allyl-5-phenyl-1,3-dioxolan-4-one and
(2S, 5S)-2-tert.-butyl-5-allyl-5-phenyl-1,3-dioxolan-4-one.

Some of the optically active dioxolanones of the formula (VI) are known (cf. Tetrahedron 40, 1313 (1984)). They can be prepared by reacting optically active dioxolanones of the formula

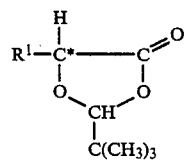  (VII)

in which
R[1] has the abovementioned meaning, with compounds of the formula $R^2-Y$  (VIII)

in which
R[2] has the abovementioned meaning and Y represents chlorine, bromine, iodine, tosylate or mesyklate, in the presence of a strong base and in the presence of a catalyst and in the presence of a diluent at temperatures between −80° C. and +80° C.

Formula (VII) provides a general definition of the optically active dioxolanones required as starting materials in the above process for the preparation of optically active dioxolanones of the formula (VI). In this formula, R[1] preferably has those meanings which have already been mentioned in connection with the description of the substances of the formula (II) as being preferred for this radical.

Some of the optically active dioxolanones of the formula (VII) are known (cf. Tetrahedron 40, 1313 (1984)). They can be prepared by reacting optically active hydroxycarboxylic acids of the formula

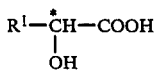  (IX)

in which
R[1] has the abovementioned meaning, with pivaldehyde of the formula

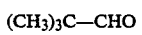  (X)

in the presence of a diluent, such as, for example, toluene, and in the presence of a catalytic amount of a strong acid, such as, for example, p-toluenesulphonic acid, at temperatures between 100° C. and 120° C.

The optically active hydroxycarboxylic acids of the formula (IX) are known or can be prepared in a simple fashion by methods which are known in principle.

Pivaldehyde of the formula (X) is likewise known.

Formula (VIII) provides a general definition of the compounds required as reaction components in the above process for the preparation of optically active dioxolanones of the formula (VI). In this formula, R[2] preferably has those meaning which have already been mentioned in connection with the description of the substances of the formula (II) as being preferred for this radical. y represents chlorine, bromine, iodine, tosylate or mesylate.

The compounds of the formula (VIII) are known or can be prepared in a simple fashion by processes which are known in principle.

Possible strong bases in the above process for the preparation of optically active dioxolanones of the formula (VI) are all deprotenation agents which are conventional for such reactions. n-Butyl-lithium may preferably be used.

Suitable catalysts in the above process for the preparation of optically active dioxolanones of the formula (VI) are all reaction accelerators which are conventional for such reactions. Basic compounds, such as diisopropylamine and bis-trimethylsilyl-amine may preferably be used.

Diluents which can be employed in the above process for the preparation of optically active dioxolanones of the formula (VI) are all solvents which are conventional for such reactions. Ethers, such as tetrahydrofuran, may preferably be used.

Formula (III) provides a definition of the tosyl halides furthermore required as starting materials when carrying out the process according to the invention. Compounds of this formula are p-tosyl chloride and p-tosyl bromide.

The tosyl halides of the formula (III), like the azoles of the formula (IV) required as reaction components in the second step of the process according to the invention, are known compounds of organic chemistry.

Possible acid-binding agents when carrying out the first step of the process according to the invention are all conventional acid acceptors. Alkali metal carbonates, such as sodium carbonate and potassium carbonate, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO), may preferably be used.

Suitable diluents when carrying out the first step of thep rocess according to the invention are all organic solvents which are conventional for such reactions. Polar organic solvents, for example nitriles, such as acetonitrile and propionitrile, and furthermore aliphatic, aromatic or heterocyclic amines, such as triethylamine, dimethylaniline, dimethylbenzylamine, pyridine, 1,5-diazabicyclo-[4,3,0]-non-5-ene, 1,8-diaza-bicyclo-[5,4,0]-undec-7-ene and 1,4-diaza-bicyclo-[2,2,2]-octane, may preferably be used.

Possible acid-binding agents when carrying out the second step of the process according to the invention are again all acid acceptors which are conventional for such reactions. Those substances which have already been mentioned as acid acceptors in connection with the description of the first step of the process according to the invention may preferably be used.

Suitable diluents when carrying out the second step of the process according to the invention are likewise all organic solvents which are conventional for such reactions. Aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as dimethyl and dibutyl ether, glycol dimethyl etherand diglycol dimethyl ether, tetrahydrofuran and dioxane, ketones such as acetone, methyl ethyl, methyl isoporopyl and methyl isobutyl ketone, esters, such as methyl and ethyl acetate, nitriles, such as, for example, acetonitrile and propionitrile, and pyridine may preferably be used.

The reaction temperatures may be varied within a relatively wide range when carrying out the process according to the invention both in the first step and in the second step. In general, the first step is carried out at temperatures between 0° C. and 100° C., preferably between 20° C. and 60° C. When carrying out the second step, temperatures between 0° C. and 150° C., preferably between 20° C. and 120° C., are generally used.

In general, the process according to the invention is carried out under atmospheric pressure. However, it is also possible to carry out both the first and the second steps under increased or reduced pressure.

When carrying out the process according to the invention, 1 to 2 moles of tosyl halide of the formula (III) and 1 to 2 moles or alternatively an excess of acid-binding agent are generally employed per mole of optically active diol of the formula (II) in the first step. In the second step, 2 to 5 moles of azole of the formula (V) and 2 to 3 mles of acid-binding agent are generally employed per mole of tosylate of the formula (IV). In detail, a procedure is followed in which optically active diol of the formula (II) is initially reacted with tosyl halide of the formula (III) in the presence of an acid-binding agent, which may also, if appropriate, function as solvent. When the reaction is complete, the reaction mixture is generally worked up by pouring into ice water, extracting the resultant mixture repeatedly with an organic solvent which is sparingly soluble in water, washing the combined organic phases successively with dilute, aqueous acid and water, and, if appropriate after prior drying, concentrating under reduced pressure.- The tosylate of the formula (IV) thus obtained is then reacted with azole of the formula (V) in the presence of an acid-binding agent. Subsequent work-up is generally carried out by pouring the reaction mixture into water, separating off the product, generally produced in solid form, and freing it from impurities still present by chromatography or other methods.

In a particular variant, the process according to the invention may be carried out as a one-pot reaction. Intermediate isolation of the tosylate of the formula (IV) is omitted in this variant.

The optically active 2-hydroxyethyl-azole derivatives of the formula (1) which can be prepared by the process according to the invention have very good fungicidal and plant growth-regulating properties (cf. EP-OS (European Published Specification) No. 0,040,345, EP-OS (European Published Specification) No. 0,052,424 and EP-OS (European Published Specification) No. 0,084,834).

The process according to the invention is illustrative by the following examples.

EXAMPLE 1

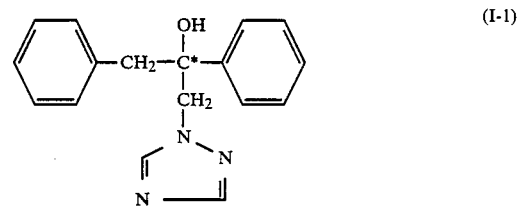

(I-1)

A mixture of 87 g (0.23 mol) of (2R)-1,2-diphenyl-2-hydroxy-3-tosyloxy-propane, 70 g (1 mol) of 1,2,4-triazole, 70 g (0.5 mol) of potassium carbonate and 800 ml of acetonitrile is refluxed for 16 hours with stirring. The reaction mixture is then poured into water, and the product which precipitates out is filtered off under suction. In order to remove any undesired biproducts which are still present, the product is dissolved in chloroform and filtered through a silica gel column, a mixture of chloroform/ethyl acetate=1:1 being used as eluent. The eluate is evaporated under reduced pressure. In this fashion, 32.5 g (51% of theory) of (2R)-1,2-diphenyl-2-hydroxy-3-(1,2,4-triazol-1-yl)-propane are obtained in the form of a solid of melting point 134° C. $[\alpha]_D^{20} = -2.7°$ (c=2.75/CHCl$_3$)

Preparation of precursors

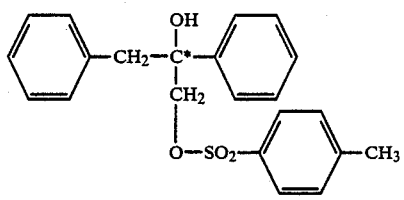
(IV-1)

66.2 g (0.35 mol) of p-tosyl chloride are added in portions with ice cooling and stirring to a solution of 63 g (0.28 mol) of (2R)-1,2-diphenyl-propane-2,3-diol in 600 ml of pyridine. The reaction mixture is allowed to stand at room temperature for 16 hours and then poured into ice water. The resultant mixture is extracted repeatedly with methylene chloride, and combined organic extracts are washed repeatedly with dilute aqueous hydrochloric acid and then with water. The organic phase is evaporated under reduced pressure. 87.2 g (83% of theory) of (2R)-1,2-diphenyl-2-hydroxy-3-tosyloxy-propane remain as a residue in the form of a solid of melting point 98° C.

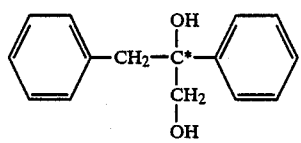
(II-1)

A solution of 90 g (0.3 mol) of (2R,4R)-2-tert.-butyl-5-benzyl-5-phenyl-1,3-dioxolan-4-one in 150 ml of ether is added dropwise to a suspension of 15.3 g (0.4 mol) of lithium aluminum hydride in 700 ml of ether with stirring at a rate such that the resultant solution refluxes gently. When the addition is complete, the mixture is refluxed for a further 1 hour. The reaction mixture is subsequently cooled using ice, and 20 ml of ice water are added slowly. As soon as the lithium aluminm hydride present has been hydrolyzed, 500 ml of water are added and the mixture is acidified using dilute aqueous hydrochloric acid. The organic phase is separated off and, after repeated washing with water, evaporated under reduced pressure. 63 g (92% of theory) of (2R)-1,2-diphenyl-propane-2,3-diol are obtained as a residue in the form of an initially oily product, which crystallizes on standing for a relatively long period. Melting point: 62° C.

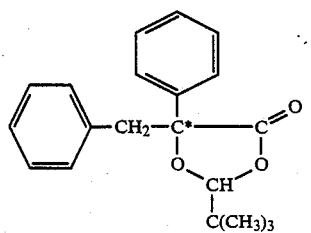
(VI-1)

144 ml (0.36 mol) of a solution of n-butyllithium in n-hexane is added dropwise to a solution of 37 g (0.36 mol) of diisopropylamine in 1 liter of absolute tetrahydrofuran at −78° C. under argon. The mixture is stirred for a further 15 minutes at −78° C., and a solution of 62.1 g (0.3 mol) of (2R,4R)-2-tert.-butyl-5-phenyl-1,3-dioxolan-5-one in 380 ml of absolute tetrahydrofuran is then added dropwise to the reaction mixture, likewise at −78° C. After stirring for a further 30 minutes at −78° C., 60.5 g (0.35 mol) of benzyl bromide are added dropwise at −78° C., and the mixture is stirred for a further one hour at this temperature. The cooling bath is subsequently removed, and the temperature of the reaction mixture allowed to increase to 20° C. The reaction mixture is hydrolyzed by slowly adding 50 ml of water. The reaction mixture is then evaporated under reduced pressure. Methylene chloride and water are added to the residue remaining. The organic phase is separated off, washed twice with water and evaporated under reduced pressure. 90 g (97% of theory) of (2R,5R)-2-tert.-butyl-5-benzyl-5-phenyl-1,3-dioxolan-4-one remain in this case as a residue in the form of an oil, which is brought to crystallization by treatment with petroleum ether. Melting point: 50° C.

The substances mentioned in the following examples are also prepared by the method specified in Example 1.

EXAMPLE 2

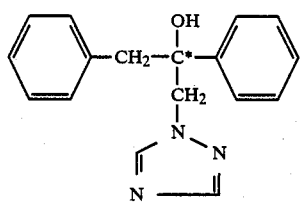
(I-2)

(2S)-1,2-Diphenyl-2-hydroxy-3-(1,2,4-triazol-1-yl)-propane

Melting point=136° C. $[\alpha]_D^{20} = +2.8°$ (c=0.537/CHCl$_3$)

EXAMPLE 3

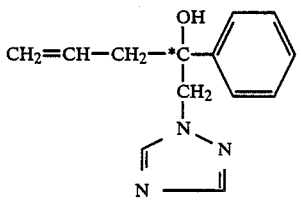
(I-3)

(4S)-4-Hydroxy-4-phenyl-5-(1,2,4-triazol-1-yl)-pent-1-ene Oil; $[\alpha]_D^{20} = +29.6°$ (c=0.692/CHCl$_3$)

EXAMPLE 4

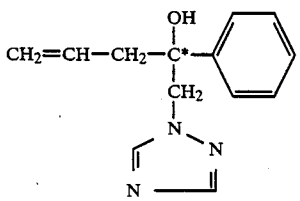
(I-4)

(4R)-4-Hydroxy-4-phenyl-5-(1,2,4-triazol-1-yl)-pent-1-ene Oil; $[\alpha]_D^{20} = 28.6°$ (c=0.765/CHCl$_3$)

It will be understood that the specification and examples are illustrative but not limitative of the present invention and that other embodiments within the spirit and scope of the invention will suggest themselves to those skilled in the art.

I claim:

1. A process for the preparation of an optically active 2-hydroxyethyl-azole derivative of the formula

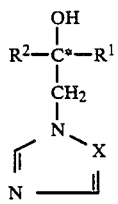
(I)

in which
R¹ represents alkyl having 1 to 6 carbon atoms, cycloalkyl having 3 to 8 carbon atoms which is optionally monosubstituted, disubstituted or trisubstituted by alkyl having 1 to 4 carbon atoms and/or halogen, the substitutents being identical or different, cycloalkylalkyl which has 3 to 8 carbon atoms in the cycloalkyl part and 1 to 4 carbon atoms in the alkyl part and which is optionally monosubstituted, disubstituted or trisubstituted by alkyl having 1 to 4 carbon atoms and/or halogen, the substituents being identical or different, or phenyl which is optionally monosubstituted, disubstituted or trisubstituted by alkyl having 1 to 6 carbon atoms, halogen, halogenoalkyl having 1 to 2 carbon atoms and 1 to 5 halogen atoms, nitro and/or hydroxyl the substituents being identical or different, R² represents straight-chain or branched alkyl having 1 to 8 carbon atoms, alkynyl having 3 to 8 carbon atoms, cycloalkyl having 3 to 8 carbon atoms, cycloalkylalkyl having 3 to 8 carbon atoms in the cycloalkyl part and 1 to 4 carbon atoms in the alkyl part, benzyl which is optionally monosubstituted, disubstituted or trisubstituted in the phenyl part by alkyl having 1 to 4 carbon atoms and/or halogen, the substituents being identical or different, or the radicals of the formulae —CH₂'CH₂—R³,CH₂—O—R³, —C≡C—R³ or —CH₂—CH═CH—R⁴, where R³ represents phenyl which is optionally monosubstituted, disubstituted or trisubstituted by alkyl having 1 to 4 carbon atoms, alkoxy having 1 to 4 carbon atoms, halogen and/or phenyl, the substituents being identical or different, and R⁴ represents hydrogen or phenyl which is optionally monosubstituted, disubstituted or trisubstituted by alkyl having 1 to 4 carbon atoms, alkoxy having 1 to 4 carbon atoms, halogen and/or phenyl, the substituents being identical or different, and X represents a nitrogen atom or a CH group, comprising (a) in a first stage, reacting an optically active diol of the formula

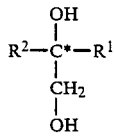
(II)

with a tosyl halide of the formula

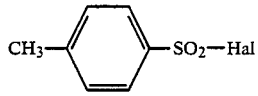
(III)

in which
Hal represents chlorine or bromine, in the presence of an acid-binding agent, thereby to produce a tosylate of the formula

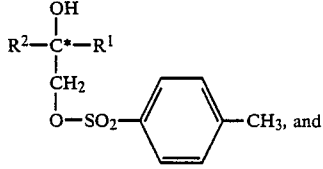
(IV)

(b) in a second stage reacting the tosylate with an azole of the formula

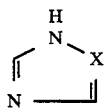
(V)

in the presence of an acid-binding agent.

2. A process according to claim 1, in which
R¹ represents alkyl having 1 to 4 carbon atoms, cycloalkyl having 3 to 6 carbon atoms which is optionally monosubstituted, disubstituted or trisubstituted by methyl, ethyl, fluorine, chlorine and/or bromine, the substituens being identical or different, cycloalkylalkyl which has 3 to 6 carbon atoms in the cycloalkyl part and 1 to 3 carbon atoms in the alkyl part and which is optionally monosubstituted, disubstituted or trisubstituted by methyl, ethyl, fluorine, chlorine and/or bromine, the substituents being identical or different, or phenyl which is optionally monosubstituted, disubstiituted or trisubstituted by alkyl having 1 to 4 carbon atoms, fluorine, chlorine, bromine, trichloromethyl, trifluoromethyl, nitro and/or hydroxyl, the substituents being identicla or different, and R² represents straight-chain or branched alkyl having 1 to 6 carbon atoms, alkynyl having 3 to 6 carbon atoms, cycloalkyl having 3 to 6 carbon atoms, cycloalkylalkyl having 3 to 6 carbon atoms in the cycloalkyl part and 1 to 3 carbon atoms in the alkyl part, benzyl which is optionally monosubstituted, disubstituted or trisubstituted in the phenyl part by methyl, ethyl, isopropyl, tert.-butyl, fluorine, chlorine and/or bromine, the substituents being identical or different, or the radicals of the formulae —CH₂—CH₂—R³, —CH₂—O—R³, —C≡C—R³ or —CH₂—CH═CH—R⁴, where R³ representd phenyl which is optionally monosubstituted, disubstituted or trisubstituted by methyl, ethyl, isopropyl, tert.-butyl, methoxy, ethoxy, fluorine, chlorine, bromine and/or phenyl, the substituents being identical or different, and R⁴ represents hydrogen or phenyl which is optionally monosubstituted, disubstituted or trisubstituted by methyl, ethyl, isopropyl, tert.-butyl, methoxy, ethoxy, fluorine, chlorine, bromine and/or phenyl, the substituents being identical or different.

3. A process according to claim 1, in which Hal is chlorine.

4. A process according to claim 1, wherein the azole of the formula (V) is 1,2,4-triazole.

5. A process according to claim 3, wherein the optically active diol is (2R)-1,3-diphenyl-propane-2,3-diol and the azole is 1,2,4-triazole.

6. A process according to claim 3, wherein the optically active diol is (2S)-1,2-diphenyl-propane-2,3-diol and the azole is 1,2,4-triazole.

7. A process according to claim 3, wherein the optically active diol is (4S)-4-phenyl-pent-1-ene-4,5-diol and the azole is 1,2,4-trizole.

8. A process according to claim 3, wherein the optically active diol is (4R)-4-phenyl-pent-1-ene-4,5-diol and the azole is 1,2,4-trizole.

9. A process according to claim 1, wherein step (a) is carried out at a temperature between 0° C. and 100° C., and step (b) is carried out at a temperature between 0° C. and 150° C.

* * * * *

UNITED STATES PATENT AND TRADEMARK OFFICE
CERTIFICATE OF CORRECTION

PATENT NO. : 4,876,353
DATED : October 24, 1989
INVENTOR(S) : Udo Kraatz

It is certified that error appears in the above-identified patent and that said Letters Patent is hereby corrected as shown below:

| | |
|---|---|
| Col. 11, line 43 | Delete "$-CH_2 \cdot CH_2-R^3,$" and substitute ---$CH_2-CH_2-R^3$-- |
| Col. 12, line 42 | Delete " disubstiituted " and substitute -- disubstituted -- |
| Col. 12, line 46 | Delete " identicla " and substitute -- identical -- |
| Col. 13, line 6 | Delete " (2R)-1,3- " and substitute -- (2R)-1,2- -- |

Signed and Sealed this

Fourth Day of June, 1991

Attest:

HARRY F. MANBECK, JR.

Attesting Officer

Commissioner of Patents and Trademarks